United States Patent [19]  
Pope, Jr. et al.

[11] Patent Number: 4,715,378  
[45] Date of Patent: Dec. 29, 1987

[54] BALLOON CATHETER

[75] Inventors: J. Lee Pope, Jr., Attleboro; Ronald E. Resden, Norton, both of Mass.

[73] Assignee: Mansfield Scientific, Inc., Mansfield, Mass.

[21] Appl. No.: 890,819

[22] Filed: Jul. 28, 1986

[51] Int. Cl.[4] .............................................. A61M 29/02
[52] U.S. Cl. ........................................ 128/344; 604/96
[58] Field of Search .................................. 604/96–103; 128/325, 343, 344, 348.1

[56] References Cited

U.S. PATENT DOCUMENTS

| | | | |
|---|---|---|---|
| 3,467,101 | 9/1969 | Fogarty et al. | 128/348.1 |
| 3,572,315 | 3/1971 | Cullen, II | 128/351 |
| 3,854,484 | 12/1974 | Jackson | 128/351 |
| 4,307,722 | 12/1981 | Evans | 128/344 |
| 4,323,071 | 4/1982 | Simpson et al. | 128/343 |
| 4,349,033 | 9/1982 | Eden | 128/660 |
| 4,444,188 | 4/1984 | Eazell et al. | 128/348 |
| 4,545,390 | 10/1985 | Leary | 128/772 |
| 4,561,439 | 12/1985 | Bishop et al. | 128/348.1 |
| 4,582,181 | 4/1986 | Samson | 128/344 |
| 4,638,805 | 1/1987 | Powell | 128/344 |

OTHER PUBLICATIONS

Advanced Cardiovascular Systems, Advertisement.

Primary Examiner—Dalton L. Truluck

[57] ABSTRACT

A balloon catheter having a distal balloon, and a catheter extending from the proximal end of the balloon, out of the body, forming a conduit for balloon inflation fluid, is sized and adapted, with the balloon deflated to a relatively small size, for introduction of the balloon into the body, and the balloon is adapted to be inflated to a relatively larger size by introduction of inflation fluid into the balloon for outside the body via the conduit. The balloon catheter includes a vent disposed at the distal end of the balloon for selectively venting gas above a predetermined pressure from the interior of the balloon while restricting passage of inflation fluid from the balloon at operating pressure. The vent consists of a multi-winding coil extending distally from within the balloon, interstitial spaces generally between the windings of the coil being of a predetermined size selected to permit passage therethrough of gaseous molecules above a predetermined pressure, while restricting throughpassage of larger molecules of inflation fluid.

4 Claims, 10 Drawing Figures

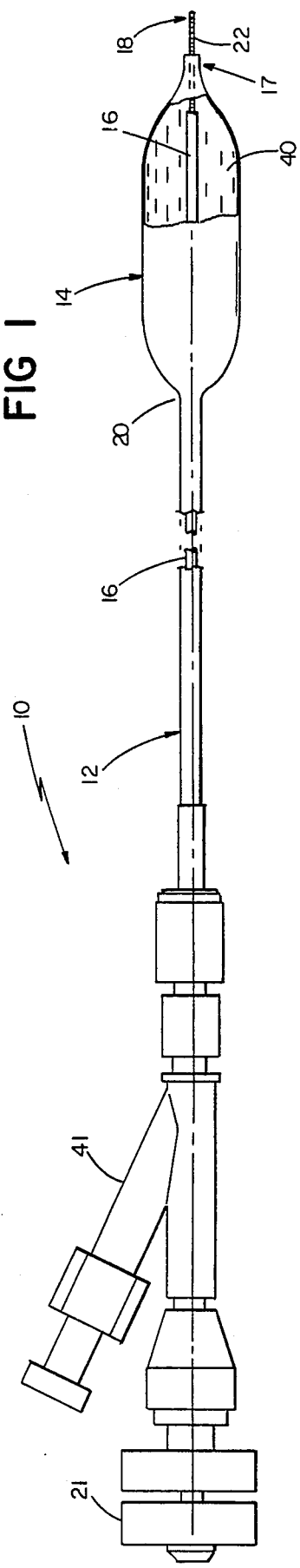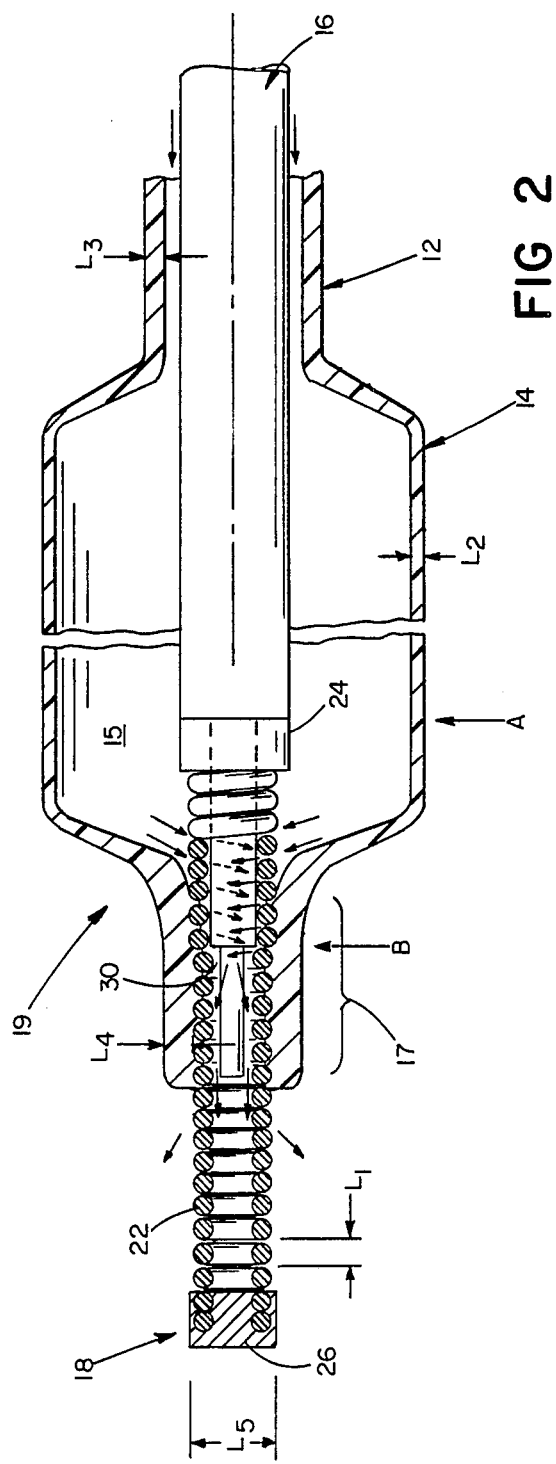

BALLOON CATHETER

BACKGROUND OF THE INVENTION

The invention relates to balloon catheters adapted for introduction into passageways and organs of the body. The catheter is typically introduced with the balloon in deflated condition for ease of insertion and to minimize the size of the opening required. Once in the desired position, the balloon is inflated by introducing fluid, i.e., liquid or gas, through the lumen of the catheter into the balloon.

In certain procedures, particularly where escape of inflating fluid within the body, e.g., due to perforation of the balloon, could adversely affect a patient's health, the fluid is carefully selected. An example is coronary angioplasty, a procedure for enlarging the flow diameter of arteries of the heart involving repeated inflation and deflation of a low profile dilatation balloon. Saline or contrast media is used as the inflating fluid because introduction of gas into the coronary arteries could be fatal. During filling of the balloon and catheter prior to commencing the procedure, all gas must be vented from the device. Samson (1986, U.S. Pat. No. 4,582,181, not conceded to be prior art to this application) uses a hypodermic tube inserted from the proximal end of the catheter to vent the air during initial filling of the system with saline or contrast media.

The objectives of this invention include providing a balloon constructed to selectively vent gas during filling with inflation fluid; providing such a balloon that may be vented without need for accessory items; providing such a balloon which can vented and prepared for insertion in much reduced time as compared to prior art devices; providing a balloon catheter of such construction, having a balloon of low profile and catheter of relatively small diameter; and providing such a balloon catheter suitable for coronary angioplasty.

SUMMARY OF THE INVENTION

According to the invention, a balloon catheter comprises a distal balloon, and a catheter extending from the proximal end of the balloon, out of the body, forming a conduit for balloon inflation fluid, the balloon catheter being sized and adapted, with the balloon deflated to a relatively small size, for introduction of the distal balloon into the body, and the balloon adapted to be inflated to a relatively larger size by introduction of inflation fluid into the balloon from outside the body via the conduit formed by the catheter, and the balloon catheter further comprises vent means disposed at the distal end of the balloon for selectively venting gas above a predetermined pressure from the interior of the balloon while restricting passage of inflation fluid from the balloon, the vent means comprising a multi-winding coil extending distally from within the balloon, interstitial spaces generally between the windings of the coil being of a predetermined small size selected to permit passage therethrough of gaseous molecules above a predetermined pressure, while restricting throughpassage of larger molecules of inflation fluid.

In preferred embodiments, the balloon catheter further comprises a guidewire extending within the catheter and terminating distally within the coil; the ballon catheter is in a form suitable for use in the procedure of percutaneous transluminal coronary angioplasty; and the interstitial spaces are of a configuration to allow the passage of air at pressure of the order of about 50 psi, and to provide sufficient restriction to flow of inflation media to enable the balloon to retain dilation pressures of the order of about 8 to 10 atm for periods of up to the order of about 1 minute.

According to another aspect of the invention, a method for forming a balloon catheter having a distal balloon, a catheter extending from the proximal end of the balloon forming a conduit for balloon inflation fluid, and a vent means disposed at the distal end of the balloon for selectively venting gas above a predetermined pressure from the interior of the balloon while restricting passage of inflation fluid from the balloon, the vent means comprising a multi-winding coil extending distally from within the balloon, interstitial spaces generally between the windings of the coil being of a predetermined small size selected to permit passage therethrough of gaseous molecules above a predetermined pressure, while restricting throughpassage of larger molecules of inflation fluid comprises the steps of placing the coil over the end of a guidewire, positioning the balloon and catheter over the guidewire and coil, with the guidewire extending proximally within the catheter, the coil extending distally from within the balloon, and the distal end of the balloon disposed loosely about the coil, proximal of the distal end of the coil, and fixing the distal end of the balloon to the coil in a manner whereby the distal end of the balloon catheter is permeable to gas molecules in said coil at pressure within the balloon above a predetermined level and are substantially impermeable to molecules of inflation fluid at operating pressure.

In preferred embodiments of the method, the distal end of the balloon is fixed about the coil by causing the material of the balloon tip to flow while applying radially inwardly directed pressure to the balloon about the coil, preferably the application of pressure is achieved by the steps of: surrounding the distal end of the balloon about the coil with a sleeve of silastic material presoaked in freon, causing the sleeve to dry to cause release of the freon and simultaneous shrinkage of the silastic sleeve to gather the balloon tip material closely about the coil, and applying heat to the balloon tip material to cause it to flow under uniform hoop pressure applied by the sleeve to seal about the coil.

Other features and advantages of the invention will be understood from the following description of a presently preferred embodiment, and from the claims.

DESCRIPTION OF THE PREFERRED EMBODIMENT

DRAWINGS

The drawings will first briefly be described.

FIG. 1 is a side view, partially in section, of a balloon catheter device of the invention;

FIG. 2 is an enlarged side section view of the distal portion of the balloon catheter device;

STRUCTURE

Figure 3:
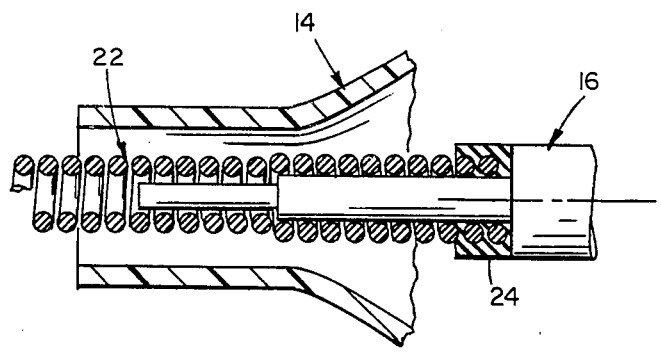
FIGS. 3, 3a and 3b are sequential side section views of the distal end of the device during formation of the vent means.

The balloon catheter device 10 of the invention, shown in FIG. 1, consists of a catheter 12 formed of a small diameter polymer tube, e.g., 0.028 inch outside diameter and 0.019 inch inner diameter, about 140 cm. long, with balloon 14 formed close to one end. Guide wire 16, e.g., 0.010 inch diameter and 157 cm. in length, extends axially through the catheter and tapers to a smaller diameter as it extends through balloon 14 to a point of attachment 17 near the distal end 18 of the device. The proximal end 20 of the balloon is attached to the distal end of catheter 12, the catheter forming a conduit for passage of inflation fluid from outside the body into and out of the balloon. Guide wire 16 is connected proximally, outside the body, to steering mechanism 21 of known construction, which is used to turn the balloon distal end 18 for passage through angular blood vessels.

Referring to FIG. 2, the distal portion of balloon catheter 10 is shown in detail. Guide wire 16 is tapered, with its outside diameter decreasing from about 0.010 inch to 0.008 inch at position A to 0.003 inch at position B; the distance from the distal tip to position B is about 1 cm., and from position B to position A is about 2 cm. Coil spring 22 has an outside diameter of, e.g., 0.015 inch and an internal diameter of, e.g., 0.009 inch and is fitted over the tapered end of guide wire 16, and fixed in position on the guide wire by means of eutectic solder 24, at the proximal end of the coil, disposed at approximately the middle of the length of the balloon. Coil spring 22 is constructed from spring coil wire of diameter, $L_1$, e.g., 0.003 inch, with at least 340 turns per inch.

Solder or a gold braze is also placed on the distal tip of the spring coil to provide a smooth introduction surface 26 of diameter, $L_5$, e.g., 0.015 inch. Balloon 14 is sealed to coil spring 22 near the balloon distal end, such that only air above a predetermined pressure can pass from volume 15 within balloon 14 through the very small interstitial spaces between the windings of the coil spring 22, as shown by the arrows, to vent from the distal end of the coil. The interstitial spaces are so small as to restrict passage of liquid through these interstitial spaces, extending over region 17, along the path shown by the arrows, both between coil spring 22 and guide wire 16, and between the coil spring and balloon 14.

Balloon 14 is formed by locally expanding the tubing forming the catheter to an outer diameter of, e.g., for use in coronary angioplasty, about 2 mm, with a wall thickness of $L_2$, e.g., 0.0014 inch. At distal end 28, the wall thickness, $L_4$, of balloon 14 is of the order of about 0.005 to 0.006 inch, slightly greater than the wall thickness $L_3$, of the catheter.

MANUFACTURE

Figure 3A:
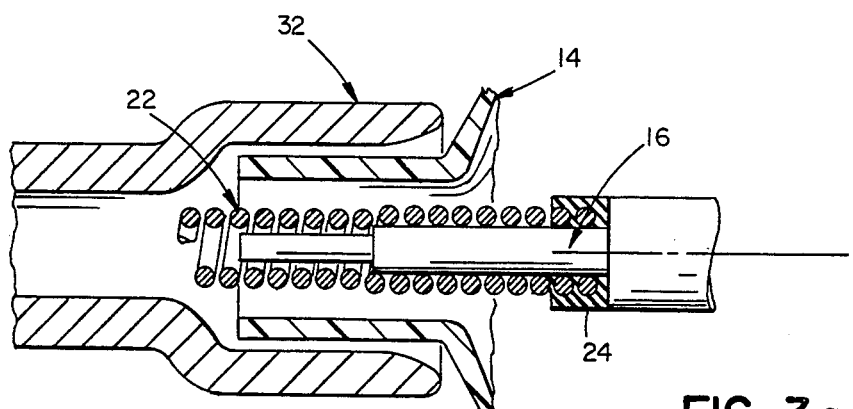
Figure 3B:
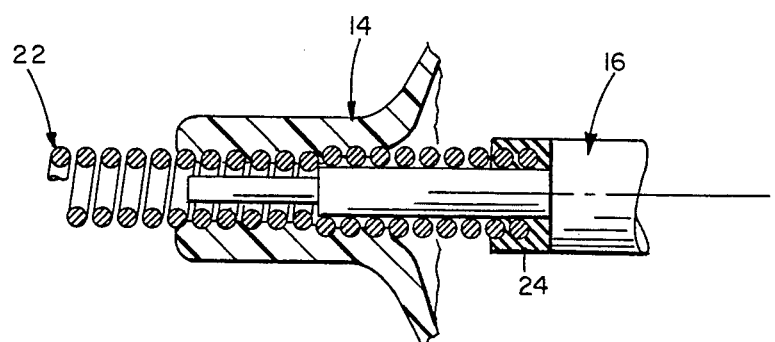

Referring to FIGS. 2, and to FIGS. 3, 3a and 3b, the process for forming the air venting interstitial spaces in region 17 at the distal end of the balloon catheter will now be described.

To manufacture balloon catheter 10, the coil spring 22 and guidewire 16 are inserted proximally through the balloon 14 and catheter 12 until the distal end 19 of the ballon is disposed about the coil, with the end of the coil extending distally. A silastic sleeve 32 of internal diameter of about 0.010 inch (FIG. 3a) is pre-soaked in freon to cause it to expand to an internal diameter of about 0.040 inch. The expanded sleeve is placed over the distal end 19 of balloon 14 disposed about coil 22 and guidewire 16 (FIG. 3). The assembly is allowed to air dry, causing release of the freon, with shrinkage of the silastic sleeve to its original diameter, gathering the balloon material tightly about the coil. The balloon tip material is then heated with a hot air gun, with the silastic sleeve still in place, to a temperature, e.g. in the range of 300° to 350° F. The material of the balloon tip decreases in viscosity to flow under the uniform hoop pressure applied by the silastic sleeve causing it to seal around the coil (FIG. 3b). (The inflatable portion of balloon 14 is protected from the heat during this process to prevent melting.) The silastic sleeve is then removed by briefly dipping the balloon tip into freon to enlarge the sleeve, which can then be reused.

This process forms the interstitial spaces between the coil windings in area 17, without sealably engaging the coil to the balloon catheter, unlike prior art devices. Adhesives are not used, nor are they necessary.

USE

Figure 4:
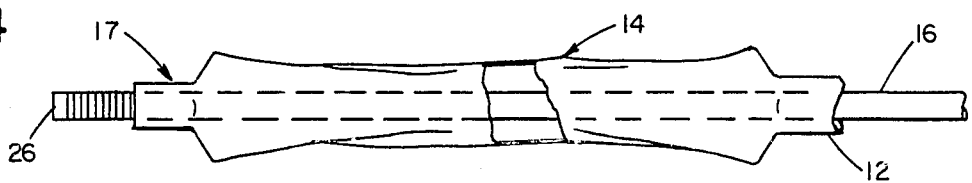
FIGS. 4, 4a, 4b, 4c, and 4d are sequential side section views of the distal portion of the balloon catheter device during an angioplasty procedure.
Figure 4A:
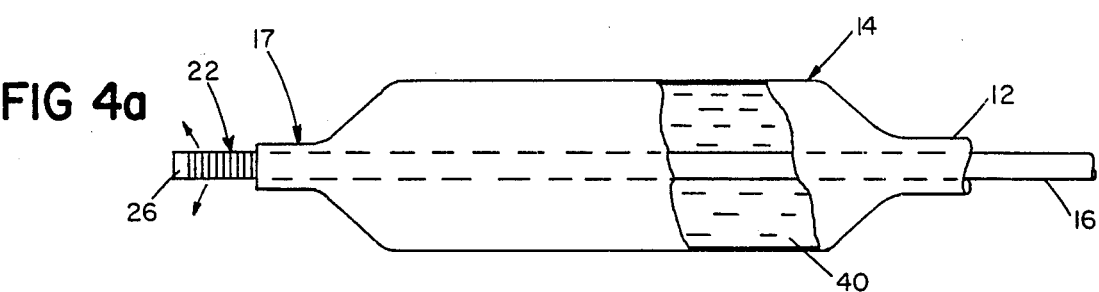

Referring to FIG. 4 et seq., the balloon catheter device 10 of the invention is provided with balloon 14 tightly wrapped around guide wire 16. Fluid 40, e.g., contrast medium, is introduced through catheter 12 into balloon 14 (FIG. 4a) using a syringe or its equivalent, and the balloon catheter oriented to cause any air remaining in the balloon to be collected at the distal end of the balloon where it is vented according to the invention via the interstitial spaces between the windings of the coil in the region indicated at 17 (shown by arrows). The interstitial spaces allow venting of air from the ballon at a pressure of approximately 50 psi, but provide sufficient restriction to flow of the much higher viscosity contrast media to enable the balloon to retain dilatation pressures of 8-10 atm. for the required period (approximately 1 minute). A slight seepage of media may be visible at the distal end of the balloon when dilatation pressures are applied, but this will not adversely affect the patient.

Figure 4B:
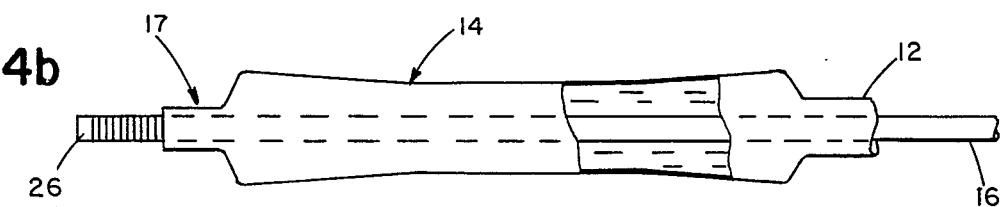

The inflation fluid is withdrawn by drawing vaccuum with a syringe attached to the proximal end 41 of catheter device 10 (not shown), so that the balloon 14 can again be tightly wrapped around guide wire 16 (FIG. 4b), but now with fluid 40 within the balloon 14 and catheter 12, in place of all air. (The deflation pressure is not so great as to cause air to be drawn back into the balloon via the interstitial spaces.)

Figure 4C:
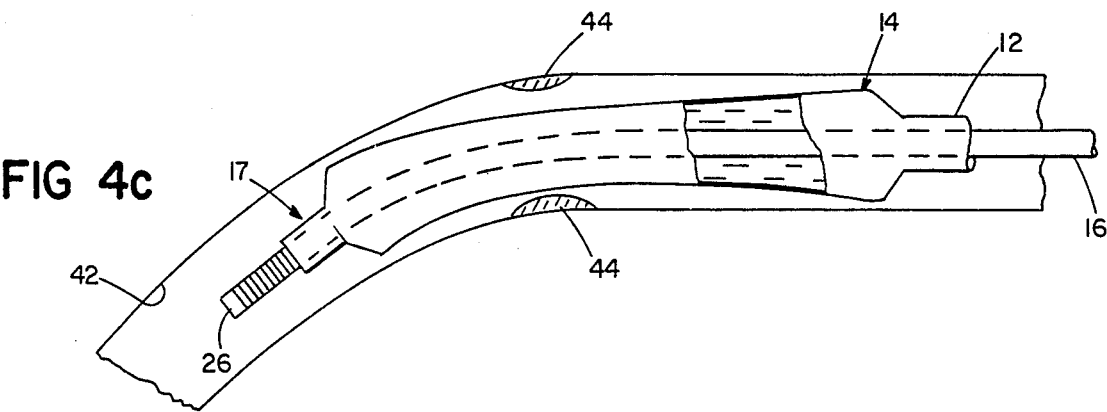
Figure 4D:
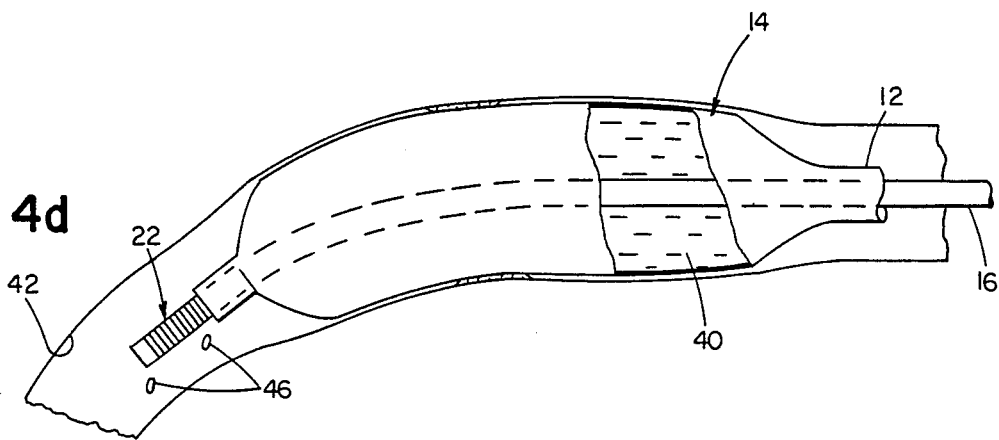

The balloon catheter is introduced percutaneously by standard procedure into blood vessel 42 (FIG. 4c) until the balloon 14 is positioned next to lesion 44 in vessel 42. The balloon is then inflated using fluid 40 until dilatation pressures (8-10 atm.) are reached. (At this pressure weeping drops 46 of inflation fluid may appear at the distal end of the device, but since fluid 40 is not harmful, this weeping is acceptable.) Dilatation fluid 40 is removed from the catheter device, using a syringe, to deflate the balloon, and the catheter device is moved for treatment at another location, or it is withdrawn from vessel 42.

Other embodiments are within the following claims.

We claim:

1. A balloon catheter, comprising:
    a distal balloon, and
    a catheter extending from the proximal end of the balloon, out of the body, forming a conduit for balloon inflation liquid,
    said balloon catheter sized and adapted, with said balloon deflated to a relatively small size, for introduction of said distal balloon into the body, and said balloon adapted to be inflated to a relatively larger size by introduction of inflation liquid into said balloon from outside the body, via the conduit formed by said catheter, and said balloon catheter further comprising vent means disposed at the distal end of said balloon for selectively venting gas above a predetermined pressure from the interior of said balloon and restricting passage of inflation liquid from said balloon, said vent means comprising a multi-winding coil extending distally from within said balloon, interstitial spaces generally between the windings of said coil being of a predetermined small size selected to permit passage therethrough of gaseous molecules above a predetermined pressure and to restrict throughpassage of larger molecules of inflation liquid at operating pressure.

2. The balloon catheter of claim 1 further comprising a guidewire extending within said catheter, said guidewire terminating distally within the said coil.

3. The balloon catheter of claim 1 of a form suitable for use in the procedure of percutaneous transluminal coronary angioplasty.

4. The balloon catheter of claim 1 wherein said interstitial spaces are of a configuration to allow the passage of air at pressure of the order of about 50 psi, and to provide sufficient restriction to flow of inflation liquid to enable said balloon to retain dilation pressures of the order of about 8 to 10 atm for periods of the order of up to about 1 minute.

* * * * *